United States Patent [19]

Molko et al.

[11] Patent Number: 5,721,341
[45] Date of Patent: Feb. 24, 1998

[54] DERIVATIVES OF NUCLEOSIDES, PROCESSES FOR THE PRODUCTION OF THESE DERIVATIVES OF NUCLEOSIDES AND SPECIFIC POLYCLONAL AND MONOCLONAL ANTIBODIES OF THESE DERIVATIVES

[75] Inventors: Didier Molko, Tullins; Jean Cadet, Cognin; Isabelle Cimaz, Grenoble, all of France

[73] Assignees: Commissariat a l'Energie Atomique; Centre National d'Etudes Spatiales, both of Paris, France

[21] Appl. No.: 605,134

[22] PCT Filed: Sep. 12, 1994

[86] PCT No.: PCT/FR94/01070

§ 371 Date: Jun. 5, 1996

§ 102(e) Date: Jun. 5, 1996

[87] PCT Pub. No.: WO95/07907

PCT Pub. Date: Mar. 23, 1995

[30] Foreign Application Priority Data

Sep. 13, 1993 [FR] France ................. 93 10864

[51] Int. Cl.$^6$ ............... C07K 16/00; C07K 5/00; C07K 7/00; C12P 21/08
[52] U.S. Cl. .......... 530/387.1; 530/300; 530/350; 530/324; 530/388.1; 530/388.9; 530/362; 530/363; 530/388.21; 530/389.8; 530/389.1; 544/118; 544/123; 435/333
[58] Field of Search .................. 544/118, 123; 530/388.21, 389.8, 389.1, 300, 350, 324, 362, 363, 387.1, 388.1, 388.9; 435/333

[56] References Cited

U.S. PATENT DOCUMENTS 5,382,580 1/1995 Chen et al. .................... 514/118

OTHER PUBLICATIONS

Erlanger et al PNAS, USA vol. 52 p. 68, Jul. 1964.
Degan et al, Carcinogensis vol. 12 p. 865, 1991.

*Primary Examiner*—Sheela Huff
*Attorney, Agent, or Firm*—Oblon, Spivak, McClelland, Maier & Neustadt, P.C.

[57] ABSTRACT

The invention relates to derivatives of nucleosides, processes for the production of these derivatives of nucleosides, as well as specific polyclonal and monoclonal antibodies of the aforementioned derivatives.

These derivatives comply with the following chemical formula:

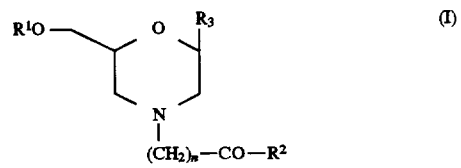

in which n is equal to 1, $R^1$ stands for H or a linear mono-, di- or tri-phosphoric acid, $R^2$ stands for a hydroxyl group, alkyl group, aryl group, a protein containing a free amino site, an aminoalkyl polystyrene or a silica grafted with an alkyl amine chain and $R^3$ represents a substituted base chosen from among uracil, thymine, cytosine, guanine or adenine.

12 Claims, No Drawings

DERIVATIVES OF NUCLEOSIDES, PROCESSES FOR THE PRODUCTION OF THESE DERIVATIVES OF NUCLEOSIDES AND SPECIFIC POLYCLONAL AND MONOCLONAL ANTIBODIES OF THESE DERIVATIVES

The invention relates to derivatives of nucleosides, processes for the production of these derivatives of nucleosides, as well as specific polyclonal and monoclonal antibodies of the aforementioned derivatives.

The macromolecule DNA (deoxyribonucleic acid) is the constituent of chromosomes and different segments of this molecule form genes, which are the supports of hereditary characteristics. DNA is in the form of a double spiraled helix formed alternatively by sugar (deoxyribose) and phosphate, the spirals of the two chains being locally joined by groups of purine or pyrimidine-type, nitrogen nucleic bases. The nucleotides constituting DNA are phosphoric esters of nucleosides.

The nucleic bases of DNA of an individual (or an animal or vegetable/plant) can be modified and damaged when said individual is exposed to intense solar radiation, cosmic radiation (intercontinental flights), photosensitizers, contact with asbestos or ionizing radiation, no matter whether the latter is accidental or due to a radiotherapy treatment. These modifications of the nucleic bases of DNA can lead to a significant change to the genetic patrimony of the individual in question. It is particularly important to detect if such modifications are produced and to define the nature of the modifications which have occurred.

It would therefore be of interest to develop a determination or assaying procedure usable in patients who may have undergone DNA modifications.

Among the various assaying procedures making it possible to determine the presence of modified DNA in a sample, immunoassays consist of reacting a specific antibody of a particular DNA modification with a sample containing isolated or hydrolyzed DNA. These antibodies are generally produced by cloning.

The production of polyclonal or monoclonal antibodies firstly requires the production of specific antigens, i.e. nucleosides or nucleotides, whose nucleic bases have undergone the modifications which it is wished to detect, said nucleotides or nucleotides being connected to a large molecule, e.g. a protein. A nucleoside or nucleotide alone would be too small to be seen by the immune system. The polyclonal antibodies are then produced by a mammal which has received an injection of the said antigen, which contains a protein foreign to the mammal in question, linked with a hapten (small molecule against which it is wished to obtain the specific antibodies).

The prior art discloses methods for the immunological determination of nucleic acids. The article by Christopher P. WILD: "Antibodies to DNA alkylation adducts as analytical tools in chemical carcinogenesis", Mut. Res., 1990, 233, pp 219–233, is devoted to specific antibodies of nucleotides, whose nucleic bases have undergone modifications by alkylation. This author insists on the function of the antibodies in the immunological determinations used in epidemiological studies of human cancers and chemical carcinogenesis, due in particular to alkylating agents.

The article by B D. Stollar: "Immunochemical analyses of nucleic acids", Progress in Nucleic Acid, Research and Molecular Biology, 1992, 42, pp 39–75 also relates to the specific antibodies of nucleic acids.

Certain oxidative deficiencies of DNA have also formed the subject matter of various publications.

Thus, the article by G. J. West et al: "Radioimmunoassay of 8-hydroxyadenine" Int. J. Rad. Biol., 1982, 42, pp 481–490 describes radioimmunoassays of 8-hydroxyadenine. This DNA modification can arise following irradiation with rays.

The article by P. Degan et al "Quantitation of 8-hydroxy-2'-deoxyguanosine in DNA by polyclonalantibodies", Carcinogenesis, 1991, 12, pp 865–871 describes specific polyclonal antibodies of 8-hydroxy-2'-deoxyguanosine and 8-hydroguanine. These polyclonal antibodies can be used in immunoassays in order to rapidly isolate the two aforementioned types of modified guanosine, e.g. in a urine sample.

The article by H. L. Lewis et al "Serologic assay of DNA base damage", Rad. Res. 1978, 75 pp 305–316 describes the preparation of polyclonal antibodies and the assay of 5-hydroxymethyldeoxyuridine, obtained after ionizing radiation of thymidine.

Finally, the article by S. A. Leadon and P. C. Hanawalt, "Monoclonal antibody to DNA containing thymine glycol", Mut. Res., 1983, 112, pp 191–200 deals with monoclonal antibodies of 5,6-dihydroxy-5,6-dihydrothymine (thymine glycol) obtained after the DNA had been exposed to ionizing or near ultraviolet rays. These monoclonal antibodies were obtained by fusing myeloma cells of mice with spleen cells from the BALB-c strain, the mice having been immunized with a poly(d-thymine) oxidized by $OsO_4$ and then complexed with methylated bovine serum albumin. The tests were carried out by ELISA methods.

The article by B. F. Erlanger and S. M. Beiser "Antibodies specific for ribonucleosides and ribonucleotides and their reaction with DNA", Proc. N.A.S., USA, 1964, 52, pp 68–74 describes a coupling protocol for a nucleic acid with a carrier protein permitting the formation of an antigen usable in a rabbit immunization protocol. This coupling protocol is shown below.

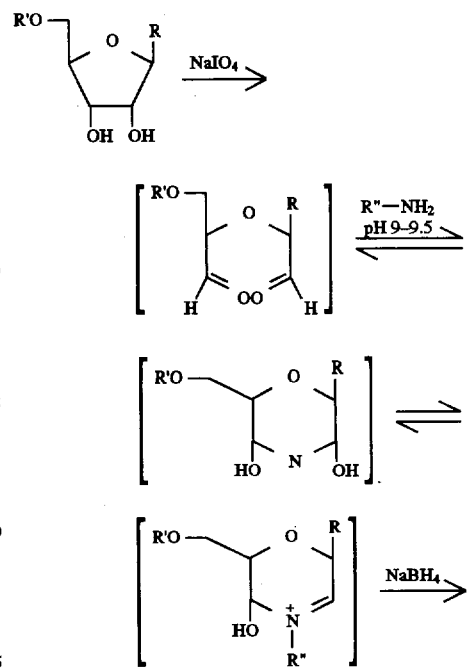

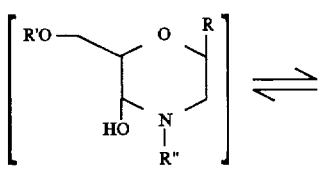

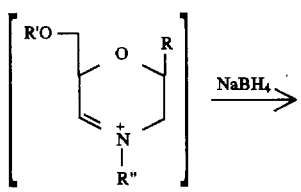

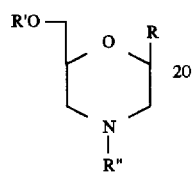

R represents a purine or pyrimidine base, R' stands for H or —PO—(OH)$_2$ and R" stands for the residue of a protein.

This process consists of acting on the monosaccharide of a ribonucleoside by the action of sodium periodate. The monosaccharide cycle is open between carbons 2' and 3' and a dialdehyde is formed. This dialdehyde is then coupled to a protein at a pH close to 9 to 9.5. NaBH$_4$ is used to reduce the Schiff's base obtained as the intermediate.

However, the process disclosed in said article is limited to nucleic bases which have not undergone modifications. Thus, with certain fragile bases sensitive to oxidation and/or reduction, it would be impossible to modify beforehand these bases of nucleosides and then make said modified nucleosides undergo an oxidation stage by sodium periodate, followed by a reduction stage using sodium hydridoborate. After such a chemical treatment, most of the defects for which it was wished to study modified DNA would have been deteriorated.

Moreover, the sequence of reactions described in this process takes place without isolating the intermediates. Consequently a certain number of parasitic products are liable to appear during the process and to be present in the final conjugate protein. Each parasitic product can potentially induce an immune reaction inherent thereto. In this case, the mixture of antibodies obtained may only have a limited selectivity. This is the case in the article by H. L. Lewis et al referred to hereinbefore, where the target molecule was 5-hydroxymethyluracil and where the antiserum obtained also recognized thymine, which is a natural base of DNA.

The article by T. Okabayashi et al "A radioimmunoassay for 1-β-D-Arabinofuranosylcytosine", Cancer Res., 1977, 17, pp 619–624 discloses a process consisting of reacting a derivative of succinic acid with a deoxynucleoside whose base has been modified, followed by the creation of an amide function with the free amine of a protein. This process is illustrated below.

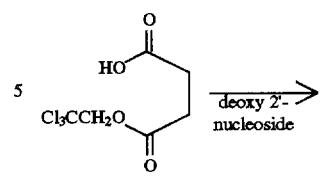

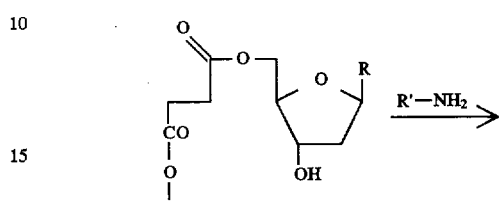

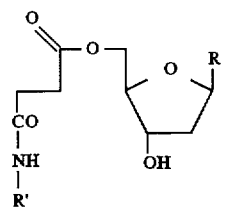

R represents a purine or pyrimidine base and R' the residue of a protein.

The main defect of this process is the lack of stability of the ester function used for conjugating the nucleoside with the protein.

An article by M. D. Friesen et al "Isolation of urinary 3-methyladenine", Chem. Res. Toxicol., 1991, 4, pp 102–106 discloses one of the most widely used methods for coupling an alkylated nucleic base to a protein and which is illustrated below.

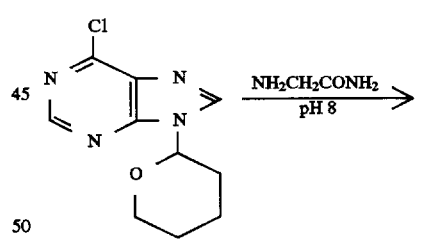

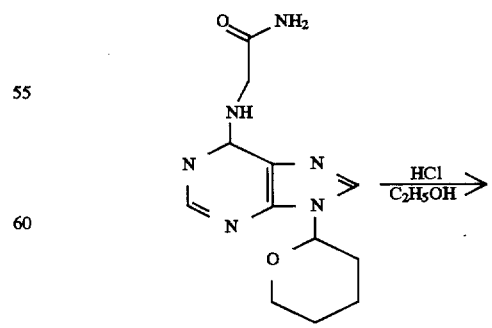

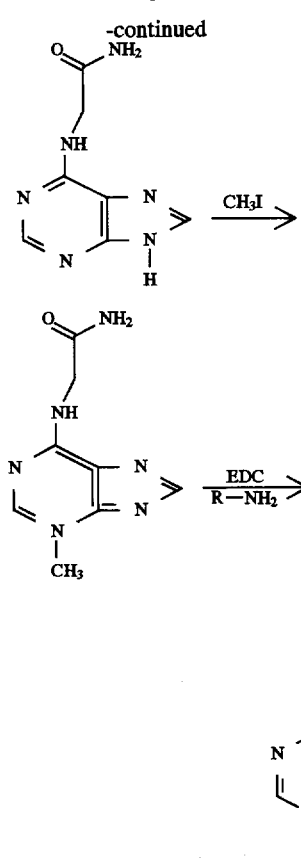

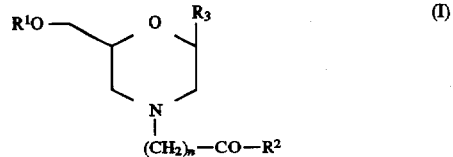

In the above R is a protein and EDC represents 1-[(3-dimethylamino)propyl]-3-ethyl dicarbodiimide hydrochloride.

This method differs from the two previous methods in that the starting product is neither a ribo- nor a deoxyribonucleoside in modified form, but is instead an alkylated derivative of the base. It makes it possible to form antibodies of excellent quality, because the hapten used is purified just prior to its conjugation with the protein. However, this procedure is more difficult to perform than the two methods described hereinbefore.

The object of the invention is to develop antigens and processes for the production of said antigens avoiding the aforementioned disadvantages.

To this end, the invention relates to derivatives of nucleosides, characterized in that they comply with the following chemical formula:

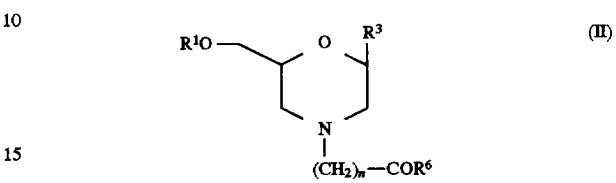

in which N is equal to one, $R^1$ stands for H or a linear mono-, di- or tri-phosphoric acid, $R^2$ is a hydroxyl group, an alkyl group, an aryl group, a protein having an amino site, an aminoalkyl polystyrene or a silica grafted with an alkyl amine chain and $R^3$ stands for a substituted base chosen from among uracil, thymine, cytosine, guanine or adenine.

The expression "derivatives of nucleosides" is used, because they are formed from nucleosides, but in said derivatives the monosaccharide has disappeared and is replaced by morpholine.

When $R^2$ represents a protein, the antigen obtained can serve as a base for antibody production.

When $R^2$ is an aminoalkyl polystyrene or a grafted silica, e.g. the product obtained is a solid support to which is linked the hapten. Such supports can be used in ELISA (registered trademark)-type determinations.

The invention also relates to a process for the production of derivatives of nucleosides complying with the following chemical formula:

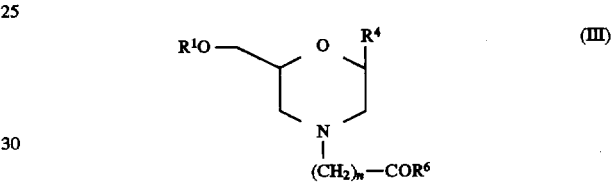

in which n represents a random positive integer, n is equal to 1, $R^1$ stands for H or a linear mono-, di- or tri-phosphoric acid, $R^6$ is a hydroxyl group, an alkyloxy group or an aryloxy group and $R^3$ a modified nucleic base chosen from among uracil, thymine, cytosine, guanine or adenine, consisting of reacting a substituent with a nucleoside derivative complying with the following general formula:

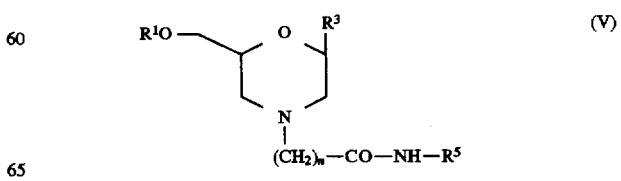

in which N is equal to 1, n represents a random positive integer, $R^1$ and $R^6$ have the same meanings as hereinbefore and $R^4$ stands for a nucleic base chosen from among uracil, thymine, cytosine, guanine or adenine.

Unlike in the prior art processes, the process according to the invention does not involve a fragile ester bond between the modified nucleoside and the protein. Therefore the conjugates obtained are much more stable and can be stored in solution without undergoing deterioration for a longer period.

The starting product (III) has a morpholine in place of the deoxyribosidic cycle. This product is stable and is also carefully purified prior to use in the process. This obviates the presence of "parasites" or contaminants in the hapten produced.

The starting product (III) has already undergone the transformation of the monosaccharide cycle into a morpholine cycle before the nucleic base is modified in the process of the invention. This makes it possible to envisage the preparation of antigens in which the nucleic bases are oxidized or reduced, which is much more difficult to obtain if the synthesis of the morpholine cycle occurs after the modification of the nucleic base.

The invention also relates to another process for the production of derivatives of nucleosides complying with the following chemical formula:

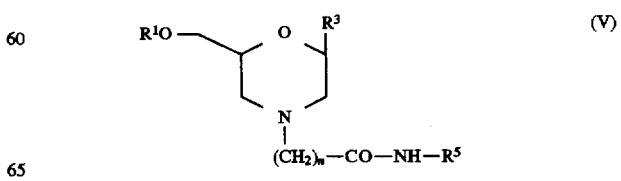

in which n is equal to 1, n represents a random positive integer, $R^1$ stands for H or a linear mon-, di- or triphosphoric acid, $R^3$ stands for a modified nucleic base chosen from among uracil, thymine, cytosine, guanine or adenine and $R^5$ represents the residue of a protein, an alkyl polystyrene or a silica grafted with an alkyl chain, said process consisting of reacting a compound of type $NH_2$—$R^5$, in which $R^5$ has the same meaning as hereinbefore with a nucleoside derivative complying with the following chemical formula:

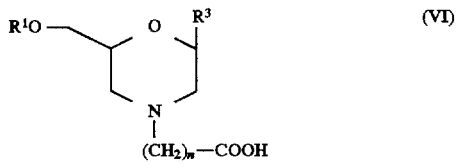

in which n, $R^1$ and $R^3$ have the same meanings as hereinbefore.

When $NH_2$—$R^5$ is a protein, the product (V) obtained is an antigen. When $NH_2$—$R^5$ is an aminoalkyl polystyrene or a silica grafted with an alkyl amine chain, the product (V) obtained is a solid support. Thus, in an ELISA determination process, the walls of the test tubes or the depressions of the plates could be covered with grafted silica, which could permit the covalent bonding of the hapten to the support.

In addition, Pharmacia markets an apparatus for dynamically studying the interactions between biological molecules (known under the registered trademark BiaCore). The principle consists of fixing one molecule to a solid support and circulating a solution containing the other. The solid support obtained according to the invention can be used in such an apparatus.

Moreover, the invention also relates to polyclonal antibodies anti-derived from nucleosides, obtained by the immunization of a suitable mammal with the antigen complying with the following chemical formula:

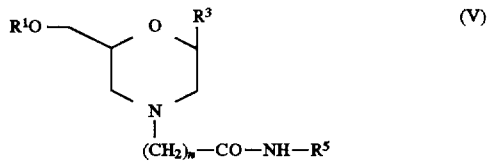

in which N is equal to 1, n represents a random positive integer, $R^1$ represents H or a linear mono-, di- or tri-phosphoric acid, $R^3$ stands for a modified nucleic base chosen from among uracil, thymine, cytosine, guanine or adenine and $R^5$ stands for a protein not obtained from said mammal.

Finally, the invention relates to monoclonal antibodies anti-derived from nucleosides obtained by fusing the myeloma cells of a mammal with the spleen cells of mice immunized with an antigen complying with the following chemical formula:

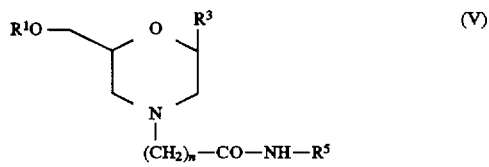

in which n is equal to 1, n represents a random positive integer, $R^1$ stands for H or a linear mono-, di- or tri-phosphoric acid, $R^3$ stands for a modified nucleic base chosen from among uracil, thymine, cytosine, guanine or adenine and $R^5$ stands for a protein not obtained from the mouse.

The invention will be better understood from the reading of the following description of an embodiment given in an exemplified and non-limitative manner.

A first process for the preparation of derivatives of nucleosides according to the invention consists of using a nucleoside or nucleoside already modified by the formation of a morpholine, so as to permit the subsequent bonding e.g. to an amino group belonging to a protein.

The starting product (III) (hereinafter called morpholinonucleoside) has the following chemical formula:

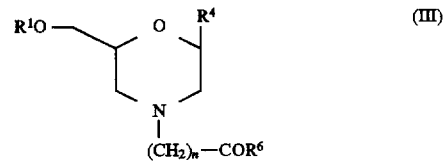

in which N is equal to 1, n represents a random positive integer, $R^1$ stands for H or linear mono-, di- or tri-phosphoric acid, $R^6$ stands for a hydroxyl group, an alkyloxy group or an aryloxy group and $R^4$ stands for a nucleic base chosen from among uracil, thymine, cytosine, guanine or adenine.

This product (III) can e.g. be obtained by a process described in the article by R. Rayford et al, "Reductive alkylation with oxidized nucleotides" J. Biol. Chem., 1985, 260, pp 15708–15713 and illustrated below:

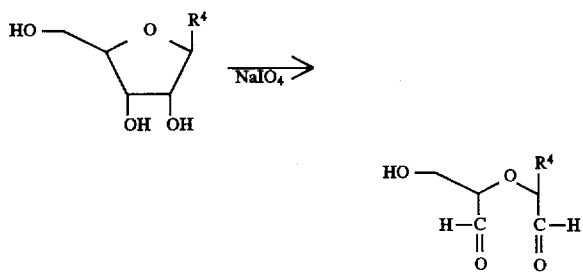

$R^4$ has the same meaning as hereinbefore.

This process consists of reacting a nucleoside with sodium periodate, in order to open the bond between the 2' carbon and 3' carbon. This gives a dialdehyde, which is reacted with glycine in order to form a double Schiff's base. This double base is reduced by $NaCNBH_3$ in order to obtain a morpholinonucleoside. The nucleoside used in the above article was adenosine. However, in similar manner, this treatment can be performed with other purine or pyrimidine bases. In the same way the nucleoside can be replaced by a nucleotide in which the phosphoric acid is in the 5 position.

When $R^6$ is an alkyl or aryl group, the product (III) is an ester. It can be obtained by the process described hereinbefore by replacing the glycine by a glycinate, such as e.g. a t-butyl or ethyl glycinate. Moreover, these derivatives can be transformed into active esters for condensing to an amine function.

The starting product (III) of the process according to the invention can also be obtained by any random other process.

The substituents making it possible to perform the substitutions on the purine or pyrimidine bases are generally agents leading to oxidative modifications of these bases. They are physical treatment or chemical agents. The chemical agents are e.g. chosen from among ozone, hydrogen peroxide, bromine combined with collidine, bromine and silver oxide, potassium permanganate, osmium tetraoxide, methanal or $AlLiH_4$. The same result could be obtained by the action of ionizing rays in the presence or absence of oxygen; by photochemistry (UV followed by photosensitizer), by catalytic hydrogenation; or by treatment with bromine and water followed by hydrogenolysis. This is followed by a summary table I of substituents and the substitutions obtained by them on different purine or pyrimidine bases.

TABLE I

| Nucleic bases | Substituent | | Substituted bases (R³) |
|---|---|---|---|
| cytosine 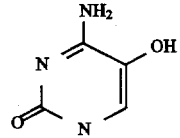 | bromine, then collidine or ionizing rays or photochemistry (UV + photosensitizer) | s | 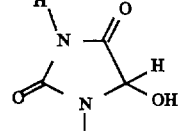 (5-hydroxycytosin)-1yl |
| | ozone or ionizing rays or photochemistry (UV + photosensitizer) | s | (5-hydroxyhydantoin)-1yl |
| | ionizing rays or photochemistry (UV + photosensitizer) | s | —NH—CO—NH—CO—NH₂ |
| uracil 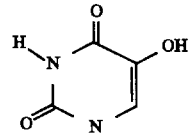 | bromine, then collidine or ionizing rays or photochemistry (UV + photosensitizer) | | (5-hydroxyuracil)-1yl |
| | H₂CO | | (5-formyluracil)-1yl |
| 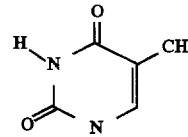 | AlLiH₄ | | 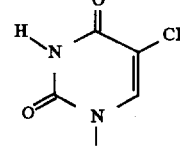 (5-hydroxymethyluracil)-1yl |
| thymine (or 5-methyluracil) 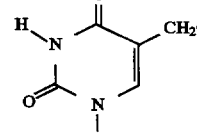 | ionizing rays or photochemistry (UV + photosensitizer) | | 5-hydroxymethyl-uracil-1yl or |

TABLE I-continued

| Nucleic bases | Substituent | Substituted bases (R³) |
|---|---|---|
| | | 5-(formyl-uracil)-1yl |
| | ozone or ionizing rays or photochemistry (UV + photosensitizer) | —NH—CHO |
| | $KM_nO_4$ or $O_sO_4$ or $Br_2$, then $Ag_2O$ or ionizing rays or photochemistry (UV + photosensitizer) | 5,6-dihydro-5,6-dihydroxythymin)-1yl |
| | hydrogen (by catalytic hydrogenation in the presence of palladium or rhodium) or photochemistry (UV + photosensitizer) | (5,6-dihydrothymin)-1yl |
| | or ionizing rays in the absence of oxygen | or (5,6-dihydro-5-hydroxythymin)-1yl |
| adenine | $H_2O_2$ | adenine-N1-oxide |
| | $Br_2 + H_2O$, then hydrogenolysis or ionizing rays or photochemistry (UV + photosensitizer) | (8-oxo-7,8-dihydroadenin)-9yl |

TABLE I-continued

| Nucleic bases | Substituent | Substituted bases (R³) |
|---|---|---|
| | ionizing rays without oxygen or photochemistry (UV + photosensitizer) | [(6-amino-5-formylamino-pyrimidin)-4yl]amino |
| guanine | Br₂, then hydrogenolysis or ionizing rays | 8-oxo-7,8-dihydroguanin-9yl |
| | ionizing rays without oxygen | [(2-amino-6-oxo-5-formylamino-pyrimidin)-4yl]amino |
| | photochemistry (V + photosensitizer) or oxygen singlet | (4,8-dihydro-4-hydroxy-8-oxo-guanin)-9yl |
| | rayonnements ionisants ou photochimie (U.V. + phososensibilisateur) | [(2,2-diamino-oxazyl-4 one)-5yl]amino |

At the end of the process according to the invention is obtained hapten with the following chemical formula:

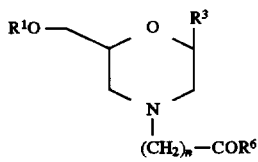

(II)

in which n is equal to 1, n represents a random positive integer, $R^1$ stands for H or a linear mono-, di- or triphosphoric acid, $R^6$ stands for a hydroxyl group, an alkyloxy group or an aryloxy group and $R^3$ is a nucleic base chosen from among cytosine, uracil, thymine, adenosine and guanine and preferably one of the modified or substituted bases of table I.

It should be noted that product II has a certain number of possible variants of product (I).

Hereinafter will be given a specific preparation example for one of these haptens.

EXAMPLE 1

Synthesis of 2-(5-hydroxycytosin)-1-yl)-4-carboxymethyl-6-(hydroxymethyl)-morpholine 100 mg of 2-(cytosin-1-yl)-4-carboxymethyl-6-hydroxymethyl morpholine are dissolved in 5 ml of water.

This is followed by the dropwise addition of bromine until the yellow colouring is maintained. After 15 minutes stirring at ambient temperature, the excess bromine is expelled by bubbling air into the solution. This is followed by the addition of 200 µl of collidine and the solution is stirred for 2 hours at ordinary temperature. The water is evaporated under reduced pressure and then the free collidine is eliminated by co-evaporation of 5 ml of ethanol. The residue obtained is analyzed by high pressure liquid chromatography (Nuclesil 10-C18 column of Macherey Nagel (registered trademark), dimensions 6×300 mm, mobile phase 50 mM triethyl ammonium acetate and methanol). Analysis reveals the presence of a majority product (60%) different from the starting product. NMR analysis of the collected product shows that it is indeed the expected compound. This product is characterized by an absorption maximum in the ultraviolet at 290.4 nm for a molar extinction coefficient of 5700 mole/l$^{-1}$ cm$^{-1}$.

The second process of the invention consists of treating the hapten (VI) obtained at the end of the first process so as to e.g. form an antigen or solid phase (film, gel) in which the hapten VI is covalently fixed to the support. This process is described below:

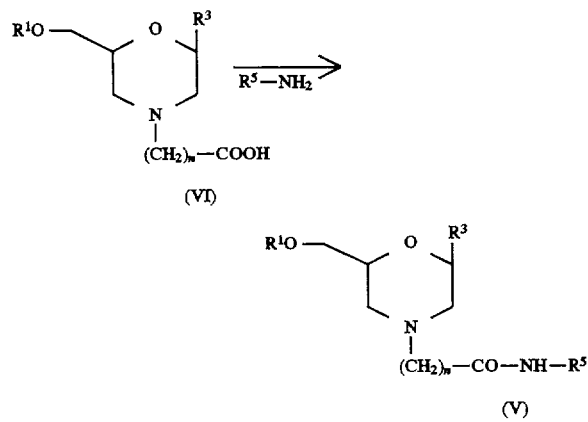

n, $R^1$ and $R^3$ have the same meanings as hereinbefore and $R^5$ represents the residue of a protein, an alkyl polystyrene or a silica grafted with an alkyl chain.

The starting hapten (VI) is purified by high pressure liquid chromatography before being coupled to the radical $NH_2$—$R^5$. The radical $R^5$ can be a protein, which is e.g. chosen from among methylated bovine serum albumin, turkey or chicken egg albumin or hemocyanins and in particular KLH or keyhole limpet helocyanin, i.e. a protein of the limpet. This gives an antigen which can be used in the production of antibodies. During the production of polyclonal antibodies, the protein will be chosen so as to be of a different nature from that of the animal used for antibody production. The aforementioned proteins are suitable when it is wished to immunize a rabbit.

The radical $NH_2$—$R^5$ can also be an aminoalkyl polystyrene or a silica grafted with an alkyl amino chain. This gives a film or a gel in which the hapten is covalently bonded to the support.

It should be noted that product (V) has a certain number of possible variants of product (I).

An example of performing the process is given below.

EXAMPLE 2

Synthesis of a hapten-protein conjugate (antigen)

300 mg (90 µmoles) of 2-(5-hydroxycytosin-1-yl)-4-carboxymethyl-6-hydroxymethylmorpholine are dissolved in 2 ml of water. This compound dissolved in water is added in 3 hours to 5 ml of a solution containing 35 mg (180 µmoles) of E.D.C. (N'-(3-dimethylaminopropyl)-N-ethyl carbodiimide (hydrochloride)) and 80 mg of bovine serum albumin. After allowing the solution to stand overnight at ambient temperature, the water is evaporated under reduced pressure and the residue obtained is dissolved in 2 ml of water and analyzed by exclusion chromatography (Fractogel TSK-HW40 (registered trademark) column of Merck, dimensions 20×400 mm, mobile phase 0.15M NaCl).

The product eluted first is collected, dialyzed against water and the solution obtained is then lyophilized. The hapten charge of the product is then measured. This measurement is obtained by comparing the UV absorption spectrum of the original protein with that of the protein grafted on the modified nucleoside. The absorption comparison at 270 and 300 nm makes it possible to establish that 7.8 moles of 2-(5-hydroxycytosin-1-yl)-4-carboxymethyl-6-hydroxymethyl morpholine are grafted per mole of protein.

The invention finally relates to the specific antibodies of antigens (V) obtained by the aforementioned process, in which $R^5$ represents the residue of a protein.

The polyclonal antibodies are obtained in conventional manner by injection into rabbits, as described hereinafter. However, the antibody obtained is novel, because it is specific to the novel, previously prepared antigen.

Hereinafter will be given an example of the preparation of these polyclonal antibodies.

EXAMPLE 3

Preparation of polyclonal antibodies specific to the antigen of example 2

The immunization protocol was based on two female rabbits of strain NZ "S.S.C." weighing 2 kg and which were treated in the manner described hereinafter.

An emulsion was prepared by mixing 1 mg/liter of the hapten-protein conjugate previously prepared in example 2, with 1 ml of complete Freund adjuvant. Each female rabbit received 1 injections of 100 µl of the aforementioned emulsion in the neck and back. Four weeks after the first injections the rabbits received a first booster under identical conditions. After a further four week interval, they received a further booster. The latter took place by intramuscular injection into the hip of 0.5 ml of an emulsion formed by 1 mg/ml of hapten-protein conjugate and 1 ml of incomplete Freund adjuvant.

Two weeks later 2 to 5 ml of blood were taken from the rabbit's ear. The collected serum made it possible to perform the first tests. Finally, four weeks after the second booster, a third booster was given by intramuscular injection using the same principle as for the second booster. Two weeks later the rabbits were killed and the maximum of their blood was collected, the serum containing the specific antibodies of the aforementioned antigen.

The monoclonal antibodies can be obtained in conventional manner by fusing myeloma cells of a mammal such as a mouse with spleen cells e.g. from the BALB/c mouse strain, said mice having been immunized with antigen (V) constituted by modified morpholino nucleoside bonded to the carrier protein ($R^5$ representing a protein). These antibodies are specific to the novel antigens obtained by the process according to the invention.

Hereinafter is given an example of the preparation of these monoclonal antibodies.

EXAMPLE 4

Preparation of monoclonal antibodies specific to the antigen of example 2 (2-(5-hydroxycytosin-1-yl)-4-carboxylmethyl-6-hydroxymethyl morpholine)

Immunization:

A suspension of the antigen of example 2 was emulsified in an identical volume of complete Freund adjuvant. This emulsion was injected intraperitoneally into female mice of strain BALB/c, aged 6 to 8 weeks and at a dosage rate of 0.1 ml of emulsion. Three weeks later, an intraperitoneal booster injection was given with an emulsion of the antigen of example 2 and incomplete Freund adjuvant. Two weeks after this booster, the final immunization took place by injection into the veins of the tail of the mouse, said injection incorporating the antigen of example 2 dissolved in 0.15M NaCl.

Cellular fusion and cloning

Three days after the final booster injection, the spleens were removed from the mice and pulverized. The spleen cells were washed in modified Dulbecco medium not containing serum (DMEM). $10^8$ spleen cells were mixed with $10^7$ myeloma cells and then centrifuged at 500×g for 7 minutes at ambient temperature. This was followed by the elimination of the medium and the recovery of the centrifuging mass, to which was added 0.8 ml of 50% PEG 4000 (Merck), over a period of 1 minute accompanied by gentle stirring at 37° C. This was followed by the addition of modified Dulbecco medium at a rate of 1 ml in 1 minute, then 20 ml for 5 minutes. The cells were centrifuged at 200×g for 10 minutes and then the centrifuging mass was resuspended in 15 ml of DMEM and 10% FBS (fetal bovine serum). 0.05 ml aliquot portions were distributed in plates proided with culture depressions coated with macrophages. The plates were allowed to incubate for 24 hours at 37° C. before adding to the depressions hypoxanthine ($1.10^{-4}$M), amethopterin ($4.10^{-7}$M) and thymidine ($1.6_4 10^{-5}$M) in DMEM (HAT medium). Seven days after fusing, addition took place of 0.025 ml of HAT medium to each depression and the medium was then replenished every 3 to 4 days. The colonies were tested by the ELISA method for their activity against the antigen of example 2. Only the cells corresponding to the positive depressions were cloned.

We claim:

1. A nucleoside derivative having the structure of chemical formula (I):

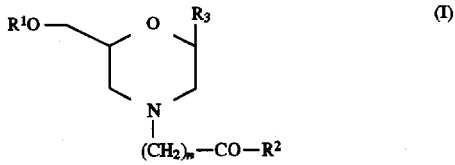

wherein n is equal to one; $R^1$ is a hydrogen or a linear mono-, di-, or tri-phosphoric acid; $R^2$ is selected from the group consisting of hydroxyl, alkyloxy, aryloxy, a protein comprising a flee amino group, an amino-alkyl polystyrene, and a silica grafted to an alkyl amine chain; and $R^3$ is selected from the group, consisting of (5-hydroxycytosin)-1-yl, (5-hydroxyhydantoin)-1-yl, —NH—CO—NH—CO—NH$_2$, (5-hydroxyuracil)-1-yl, (5-formyluracil)-1-yl, (5-hydroxymethyluracil)-1-yl, —NH—CHO, (5,6-dihydroxythymin)-1yl, (5,6-dihydrothymin)-1-yl, (5,6-dihydro-5-hydroxythymin)-1-yl, adenine-N1-oxide, (8-oxo-7,8-dihydroadenin)-9-yl, [(6-amino-5-formylamine-pyrimindin)-4-yl]amino, (8-oxo-7,8-dihydroguanin)-9-yl, [(2-amino-6-oxo-5-formylamino-pyrimidin)-4-yl]amino, (4,8-dihydro-4-hydroxy-8-oxo-guanin)-9-yl, and [(2,2-diaminooxazol-4-one)-5-yl]amino.

2. The nucleoside derivative according to claim 1, wherein the protein is selected from the group consisting of methylated bovine serum albumin, turkey albumin, chicken egg albumin, and hemocyanins.

3. A process for the preparation of a nucleoside derivative having the structure of chemical formula (II):

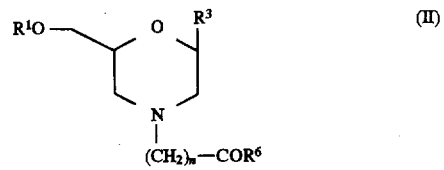

wherein n is equal to one; $R^1$ is a hydrogen or a linear mono-, di- or tri-phosphoric acid; $R^6$ is a hydroxyl group, an alkyl group or an aryl group; and $R^3$ is a substituted heterocyclic base wherein the heterocyclic base is selected from the group consisting of uracil, thymine, cytosine, guanine, and adenine, said process comprising treating a nucleoside derivative having the structure of chemical formula (III):

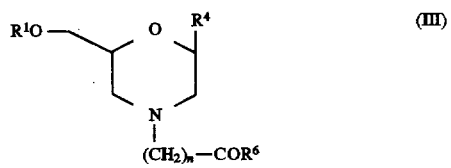

wherein n is a equal to 1; $R^1$ is a hydrogen or a linear mono-, di-, or tri-phosphoric acid; $R^6$ is a hydroxyl group, an alkyl group, or an aryl group; and $R^4$ is a heterocyclic base selected from the group consisting of uracil, thymine, cytosine, guanine, and adenine, with a chemical reaction-inducing reagent.

4. The process as claimed in claim 3, wherein the chemical reaction-inducing reagent is selected from the group consisting of ozone, hydrogen peroxide, bromine combined with collidine, bromine and Ag$_2$O, potassium permanganate, osmium, tetraoxide, methanal and AlLiH$_4$.

5. The process as claimed in claim 3, wherein the chemical reaction-inducing reagent is selected from the group consisting of ultraviolet radiation followed by a photosensitizer; ionizing rays in the presence or absence of oxygen; catalytic hydrogenation; and treatment with bromine and water followed by hydrogenolysis.

6. The process as claimed in claim 3, wherein $R^3$ is selected from the group consisting of [(5-hydroxycytosin)-1-yl, (5-hydroxyhydantoin)-1-yl, —NH—CO—NH—CO—NH$_2$, (5-hydroxyuracil)-1-yl, (5-formyluracil)-1-yl, (5-hydroxymethyluracil)-1-yl, —NH—CHO, (5,6-dihydro-5,6-dihydro-5,6-dihydroxythymin)-1-yl, (5,6-dihydrothymin)-1-yl, (5,6-dihydro-5-hydroxythymin)-1-yl, adenine-N1-oxide, (8-oxo-7,8-dihydroadenine)-9-yl, [(6-amino-5-formylamine-pyrimidin)-4-yl]-amino, (8-oxo-7,8-dihydroguanin)-9-yl, [(2-amino-6-oxo-5-formylamino-pyrimidin)-4-1]-amino, (4,8-dihydro-4-hydroxy-8-oxo-guanin)-9-yl and [(2,2-diamino-oxazol-4-one)-5-yl]-amino].

7. A process for the preparation of a nucleoside derivative having the structure of chemical formula (V):

19

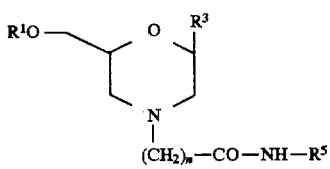

(V)

wherein n is equal to 1; $R^1$ is a hydrogen or a linear mono-, di-, or tri-phosphoric acid; $R^5$ is selected from a group consisting of a residue of a protein, an alkyl polystyrene, or a silica grafted to an alkyl chain; and $R^3$ is a substituted heterocyclic base wherein the heterocyclic base is selected from the group consisting of uracil, thymine, cytosine, guanine, and adenine, said process comprising reacting a compound of chemical structure $NH_2$—$R^5$, wherein $R^5$ is selected from the group consisting of a residue of a protein, an alkyl polystyrene, or a silica grafted to an alkyl chain, with a nucleoside derivative having the structure of chemical formula (VI):

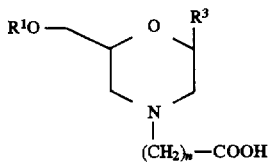

(VI)

wherein n is equal to 1; $R^1$ is a hydrogen or a linear mono-, di-, or tri-phosphoric acid; and $R^3$ is a heterocyclic base selected from the group consisting of uracil, thymine, cytosine, guanine, and adenine.

8. The process as claimed in claim 7, wherein $R^3$ is selected from the group consisting of [(5-hydroxycytosin)-1-yl, (5-hydroxyhydantoin)-1-yl, —NH—CO—NH—CO—NH$_2$, (5-hydroxyuracil)-1-yl, (5-formyluracil)-1-yl, (5-hydroxy-methyluracil)-1-yl, —NH—CHO, (5,6-dihydro-5,6-dihydro-5,6-dihydroxythymin)-1-yl, (5,6-dihydrothymin)-1-yl, (5,6-dihydro-5-hydroxythymin)-1-yl, adenine-N1-oxide, (8-oxo-7,8-dihydroadenine)-9-yl, [(6-amino-5-formylamine-pyrimidin)-4-yl]-amino, (8-oxo-7,8-dihydroguanin)-9-yl, [(2-amino-6-oxo-5-formylamino-pyrimidin)-4-1]-amino, (4,8-dihydro-4-hydroxy-8-oxo-guanin)-9-yl and [(2,2-diamino-oxazol-4-one)-5-yl]-amino].

9. A polyclonal antibody produced by immunizing a mammal with an antigen having the structure of chemical formula (V):

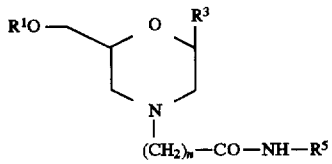

(V)

wherein n is equal to 1; $R^1$ is a hydrogen or a linear mono-, di-, or tri-phosphoric acid; $R^3$ is selected from the group consisting of (5-hydroxycytosin)-1-yl, (5-hydroxyhydantoin)-1-yl, —NH—CO—NH—CO—NH$_2$, (5-hydroxyuracil)- 1-yl, (5-formyluracil)-1-yl, (5-hydroxymethyluracil)-1-yl, —NH—CHO, (5,6-dihydro-5,6-dihydro-5,6-dihydroxythymin)-1-yl, (5,6-dihydrothymin)-1-yl, (5,6-dihydro-5-hydroxythymin)-1-yl, adenine-N1-oxide, (8-oxo-7,8-dihydroadenine)-9-yl, [(6-amino-5-formylamine-pyrimidin)-4-yl]-amino, (8-oxo-7,8-dihydroguanin)-9-yl, [(2-amino-6-oxo-5-formylamino-pyrimidin)-4-1]-amino, (4,8-dihydro-4-hydroxy-8-oxo-guanin)-9-yl and [(2,2-diamino-oxazol-4-one)-5-yl]-amino; and $R^5$ consists of a protein.

10. The polyclonal antibody according to claim 9, wherein $R^5$ is a protein selected from the group consisting of methylated bovine serum albumin, turkey albumin, chicken egg albumin, and hemocyanins.

11. A monoclonal antibody produced by the process of fusing myeloma cells of a mammal with spleen cells of a mouse immunized with an antigen having the structure of chemical formula (V):

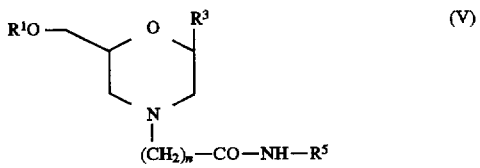

(V)

wherein n is equal to 1; $R^1$ is a hydrogen or a linear mono-, di-, or tri-phosphoric acid; $R^3$ is selected from the group consisting of (5-hydroxycytosin)-1-yl, (5-hydroxyhydantoin)-1-yl, —NH—CO—NH—CO—NH$_2$, (5-hydroxyuracil)-1-yl, (5-formyluracil)-1-yl, (5-hydroxymethyluracil)-1-yl, —NH—CHO, (5,6-dihydro-5,6-dihydro-5,6-dihydroxythymin)-1-yl, (5,6-dihydrothymin)-1-yl, (5,6-dihydro-5-hydroxythymin)-1-yl, adenine-N1-oxide, (8-oxo-7,8-dihydroadenine)-9-yl, [(6-amino-5-formylamine-pyrimidin)- 4-yl]-amino, (8-oxo-7,8-dihydroguanin)-9-yl [(2-amino-6-oxo-5-formylamino-pyrimidin)-4-1]-amino, (4,8-dihydro-4-hydroxy-8-oxo-guanin)-9-yl and [2,2-diamino-oxazol-4-one)-5-yl]-amino; and $R^5$ consists of a protein.

12. The monoclonal antibody according to claim 11, wherein $R^5$ is a protein selected from the group consisting of methylated bovine serum albumin, chicken albumin, turkey egg albumin, and hemocyanins.

* * * * *